United States Patent [19]

Takemura et al.

[11] Patent Number: 4,639,353
[45] Date of Patent: Jan. 27, 1987

[54] BLOOD OXYGENATOR USING A HOLLOW-FIBER MEMBRANE

[75] Inventors: Tohru Takemura; Atushi Nakashima, both of Ohtake; Haruhiko Yoshida, Kuga; Jun Kamo; Eiichi Hamada, both of Ohtake, all of Japan

[73] Assignee: Mitsubishi Rayon Co., Ltd., Tokyo, Japan

[21] Appl. No.: 726,391

[22] Filed: Apr. 23, 1985

[30] Foreign Application Priority Data

Apr. 24, 1984 [JP] Japan .................................. 59-81088
Aug. 7, 1984 [JP] Japan .................................. 59-164280
Nov. 9, 1984 [JP] Japan .................................. 59-236027
Nov. 9, 1984 [JP] Japan .................................. 59-236028

[51] Int. Cl.$^4$ ........................ A61M 1/14; B01D 13/01
[52] U.S. Cl. ........................................ 422/46; 422/48; 210/321.3; 128/DIG. 3
[58] Field of Search ...................... 422/46, 48; 55/158; 128/DIG. 3; 210/321.3, 321.4

[56] References Cited

U.S. PATENT DOCUMENTS

| | | | |
|---|---|---|---|
| 2,972,349 | 2/1961 | De Wall | 422/48 |
| 3,728,256 | 6/1971 | Cooper | 210/321.3 X |
| 3,998,593 | 12/1976 | Yoshida et al. | 422/46 |
| 4,188,360 | 2/1980 | Kurata | 422/46 |
| 4,231,878 | 11/1980 | Esmond | 422/48 X |
| 4,239,729 | 12/1980 | Hasegawa et al. | 128/DIG. 3 X |
| 4,272,373 | 6/1981 | Stenberg et al. | 422/48 X |
| 4,374,802 | 2/1983 | Fukasawa | 210/321.3 X |
| 4,376,095 | 3/1983 | Hasegawa | 422/46 |

Primary Examiner—Barry S. Richman
Assistant Examiner—Lynn M. Kummert
Attorney, Agent, or Firm—Oblon, Fisher, Spivak, McClelland & Maier

[57] ABSTRACT

A blood oxygenator of the outside perfusion type using hollow fibers as the gas exchange membrane. In this blood oxygenator, a plurality of contact chambers each containing a bundle or bundles of hollow fibers for gas exchange use and communicating with a blood inlet and a blood outlet are disposed to make blood flow in multiple paths within a housing, and each bundle of hollow fibers is arranged so as to be substantially perpendicular to the direction of blood flow. In spite of its compact construction, this blood oxygenator has high oxygen and carbon dioxide exchange rates per unit of membrane even when used in the gas exchange of blood having high flow rate, exhibits only a small pressure loss, and causes little channeling of the blood and gas. Moreover, it is easy to manufacture because of its relatively simple structure.

10 Claims, 9 Drawing Figures

BLOOD OXYGENATOR USING A HOLLOW-FIBER MEMBRANE

BACKGROUND OF THE INVENTION

1. Field of the Invention

This invention relates to a blood oxygenator of the outside perfusion type using a hollow-fiber membrane.

2. Description of the Prior Art

A number of blood oxygenators using hollow fibers as the gas exchange membrane have already been proposed, for example, in U.S. Pat. Nos. 2,972,349, 3,794,468, 4,239,729 and 4,374,802.

In these blood oxygenators, hollow fibers made of a homogeneous membrane of gas-permeable material such as silicone or hollow fibers made of a microporous membrane of hydrophobic polymeric material such as polyolefins are used to bring blood into contact with gas through the medium of the hollow-fiber membrane and effect gas exchange therebetween. There are two types of blood oxygenators: the inside perfusion type in which blood is passed through the bores of the hollow fibers while gas is passed on the outside of the hollow fibers and the outside perfusion type in which, conversely, gas is passed through the bores of the hollow fibers while blood is passed on the outside of the hollow fibers.

In blood oxygenators of the inside perfusion type, no channeling of the blood occurs if the blood is uniformly distributed and fed to the large number of hollow fibers. However, since the blood flowing through the bores of the hollow fibers moves in a perfect laminar flow, the internal diameter of the hollow fibers needs to be reduced in order to increase the oxygenation rate (i.e., the oxygen transfer rate per unit area of membrane). For this purpose, hollow fibers having an internal diameter of 150 to 300 $\mu$m have actually been developed for use in blood oxygenators.

Nevertheless, even if the internal diameter is reduced, the laminar flow phenomenon of the blood passing through the hollow fibers is not mitigated and the oxygenation rate of a blood oxygenator of this type is not greatly enhanced. Moreover, as the internal diameter becomes smaller, clotting (i.e., blockade of the bore due to the coagulation of blood) may occur more frequently, thus posing a serious problem for a practical point of view. Furthermore, a blood oxygenator generally uses ten thousand to forty thousand hollow fibers made into a bundle or bundles and it is very difficult to distribute and feed the gas uniformly to the external surfaces of such a large number of hollow fibers, so that special consideration must be given to achieve the desired end. If the gas is not distributed uniformly, the carbon dioxide desorption rate (i.e., the carbon dioxide transfer rate per unit area of membrane) will be reduced. On the other hand, in blood oxygenators of the outside perfusion type, the gas can be distributed uniformly and the blood can be expected to move in a turbulent flow. However, they have the disadvantage of being subject to insufficient oxygenation due to channeling of the blood or blood coagulation at the sites of stagnation. Thus, no blood oxygenator having satisfactory performance has been realized as yet.

In most of the conventionally known blood oxygenators, a cylindrical housing is simply packed with a large number of hollow fibers for gas exchange use in such a way that the hollow fibers are parallel to the longitudinal axis of the cylindrical housing. However, blood oxygenators of this construction have low gas exchange rate per unit area of the hollow-fiber membrane. As an improved form of the outside perfusion type, U.S. Pat. No. 3,794,468 has proposed a blood oxygenator in which hollow tubular conduits of semipermeable membrane are wound about a hollow, cylindrical core having a large number of pores in the wall and then contained in a housing, and blood is allowed to flow out of the cavity of the core through its pores while gas is passed through the bores of the hollow tubular conduits. However, this blood oxygenator is disadvantageous in that the priming blood volume is unduly large and the manufacture thereof requires a complicated procedure because of its intricate structure. Thus, it has not yet been put to practical use.

The conventionally known blood oxygenators in which the hollow fibers are disposed so as to be substantially perpendicular to the direction of blood flow can produce more marked turbulences of the blood flow and hence an improvement in oxygenation rate, as compared with those in which the hollow fibers are disposed so as to be parallel to the direction of blood flow. However, if the size of such a blood oxygenator is magnified or the flow rate of blood is increased in order to treat large volumes of blood, there arise such problems as an increase in pressure loss, channeling of the blood and blood coagulation at the sites of stagnation. The prior art has been unable to solve these problems.

SUMMARY OF THE IVENTION

It is an object of the present invention to provide a blood oxygenator of the outside perfusion type which has high oxygenation rate and carbon dioxide desorption rate, causes little stagnation or channeling of the blood, and exhibits only a small pressure loss.

It is another object of the present invention to provide a blood oxygenator of compact construction which can be manufactured without requiring any troublesome procedure and can be used with excellent handling properties.

It is still another object of the present invention to provide a blood oxygenator of the outside perfusion type in which gas bubbles are scarcely retained in the blood.

According to the present invention, there is provided a blood oxygenator comprising (1) a housing having a blood inlet, a blood outlet, a gas inlet and a gas outlet, the housing having formed therein (a) a plurality of contact chambers through which blood flows which form multiple channels constituting at least one half the length of the blood flow path from the blood inlet to the blood outlet and (b) gas passages, each of the contact chambers communicating with the blood inlet and the blood outlet; and (2) a bundle or bundles of hollow fibers for gas exchange use disposed in each of the contact chambers so as to be substantially rectilinear and substantially perpendicular to the direction of blood flow, the opposite open ends of the hollow fibers communicating with the gas inlet and the gas outlet through the medium of the gas passages.

DETAILED DESCRIPTION OF THE PREFERRED EMBODIMENTS

The blood oxygenator of the present invention will be more fully described with reference to the accompanying drawings.

Figure 1:
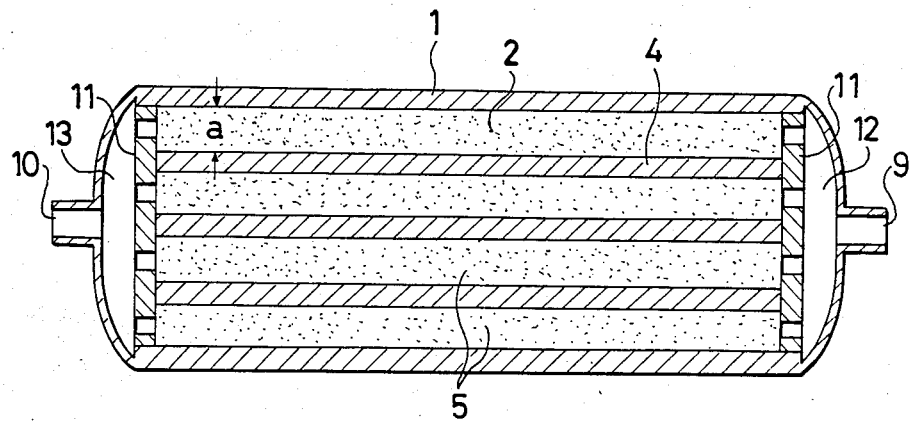
FIG. 1 is a longitudinal sectional view of one embodiment of the blood oxygenator of the present invention.
Figure 2:
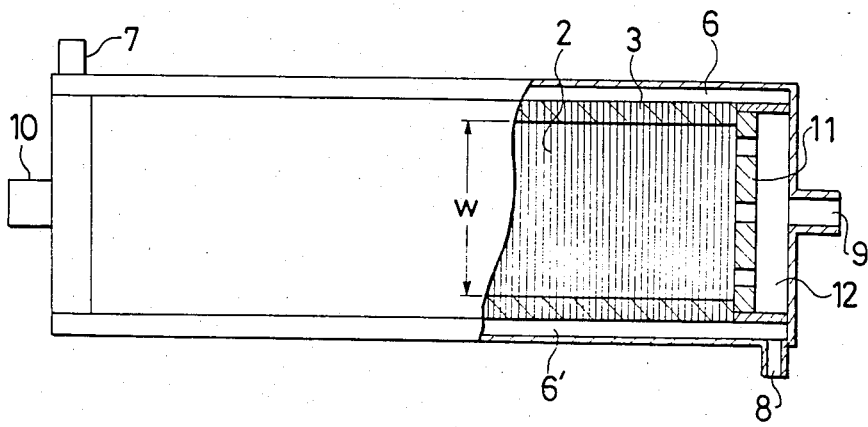
FIG. 2 is a partially cutaway plan view of the blood oxygenator of FIG. 1.

The blood oxygenator shown in FIGS. 1 and 2 comprises a housing 1 constituting its main body, hollow fibers 2, fastening members 3 and partitioning members 4. These members divide the cavity of the housing 1 into a plurality of contact chambers 5 comprising a plurality of spaces disposed in stacked relationship and allowing blood to flow therethrough, and gas passages 6, 6' for feeding an oxygen-containing gas to the bores of the hollow fibers 2. The housing 1 is provided with a gas inlet 7, a gas outlet 8, a blood inlet 9 and a blood outlet 10.

The hollow fibers 2 are disposed in each contact chamber 5 so as to be substantially rectilinear and fixed by two opposite fastening members 3 in such a way that their respective ends remain open to the gas passages 6, 6'. Each of the contact chambers 5 through which blood flows is divided into a plurality of spaces arranged in parallel, by means of the partitioning members 4 which are fixed by the fastening members 3 similarly to the hollow fibers 2. Moreover, in order to distribute and feed blood uniformly into each contact chamber and among the contact chambers, a distribution plate 11 joined to the housing 1, the fastening members 3 and the partitioning members 4 may be provided between the blood distribution chamber 12 (or 13) and the contact chambers 5.

In this blood oxygenator, an oxygen-containing gas is fed through the gas inlet 7 to the gas passage 6 within the housing 1 and then passed through the bores of the hollow fibers 2 disposed in the contact chambers 5, where it undergoes gas exchange with the blood through the medium of the hollow-fiber membrane. The gas thus decreased in oxygen content and increased in carbon dioxide content is conducted to the gas passage 6' and then discharged through the gas outlet 8. Of course, the oxygen-containing gas fed through the gas inlet 7 may comprise pure oxygen.

On the other hand, blood withdrawn from a human body (i.e., venous blood) is introduced through the blood inlet 9 into the blood distribution chamber 12 within the housing 1 and then fed to the contact chambers 5 through the slits of the distribution plate 11. In the contact chambers 5, the venous blood flows in a direction substantially perpendicular to the hollow fibers 2, comes into contact therewith, and undergoes gas exchange, through the medium of the hollow-fiber membrane, with the oxygen-containing gas flowing through the bores of the hollow fibers 2. Thus, the venous blood is converted into arterial blood, which is conducted through the blood collection chamber 13 and discharged out of the blood oxygenator through the blood outlet 10.

In the embodiment shown in FIG. 1, the contact chambers 5 comprise four spaces separated by three partitioning members 4. However, there may be present any desired number of contact chambers 5, provided that the number of contact chambers 5 is not less than two. In this blood oxygenator, the thickness (a) of each contact chamber (i.e., the distance between the adjacent partitioning members or between the partitioning member and the housing) has an important significance. In order to prevent channeling of the blood or formation of stagnation sites, produce turbulences of the blood flow within the contact chambers, and enhance the gas exchange efficiency of the blood, it is desirable that the thickness (a) of each contact chamber is as small as possible. However, if the thickness (a) is unduly small, a large number of partitioning members will be required to result in a blood oxygenator which involves a considerable pressure loss and is hard to assemble. Thus, from a practical point of view, the thickness (a) should preferably be determined so as to be of the order of 5 to 50 mm. If the thickness (a) of each contact chamber is unduly large, it will become difficult to prevent channeling or stagnation of the blood within the contact chamber, so that the objects of the present invention cannot be accomplished.

One method for reducing the thickness (a) of the contact chambers and increasing the flow rate of blood is to increase the width (w) of the contact chambers (i.e. the distance between the two fastening members). However, in order to produce a desirable highly gas-exchangeable flow of blood in each contact chamber, it is preferable that the width (w) of each contact chamber is about 5 to 60 times the thickness (a) thereof. If the width (w) is smaller than 5 times the thickness (a), the surfaces of the fastening members may exert a significant effect on the blood flow and produce an undesirable result. If the width (w) is larger than 60 times the thickness (a), it will become difficult to distribute the blood uniformly over the surfaces of all hollow fibers and thereby prevent channeling of the blood. Moreover, the housing will have such an unduly large width that difficulties may be encountered in the manufacture and use thereof.

In the blood oxygenator of the present invention, the hollow fibers are disposed in the contact chambers so as to be substantially perpendicular to the direction of blood flow. The term "direction of blood flow" as used herein does not mean the direction of the blood flow actually produced by passing blood through the contact chambers, but the direction of the straight line connecting the blood inlet of each contact chamber with the blood outlet thereof. In order to prevent channeling of the blood, the hollow fibers need to form an angle of at least 45° with the direction of blood flow, and it is most preferable that the hollow fibers are substantially perpendicular to the direction of blood flow. Moreover, the hollow fibers contained in each contact chamber are preferably disposed in such a way that, as shown in FIG. 2, they are substantially rectilinear and parallel to one another. However, the hollow fibers may also be disposed in such a way that they are formed into bundles and each bundle of hollow fibers is twisted about its longitudinal axis at an angle of up to about 45°.

In the blood oxygenator of the present invention, the degree of packing of the hollow fibers contained in each contact chamber preferably ranges from 10 to 55% and more preferably from 20 to 40%. The term "degree of packing" as used herein means the proportion of the total cross-sectional area of the hollow fibers to the cross-sectional area of the contact chamber, as viewed in a plane parallel to the direction of blood flow in the contact chamber. If the degree of packing is less than 10%, channeling of the blood will tend to occur, while if it is greater than 55%, the flow resistance of the blood may become unduly high and hemolysis may be induced.

In order to improve the functionality (i.e., gas exchange capacity) of a blood oxygenator, it is important to reduce the thickness of its contact chamber. However, if the thickness is reduced, the cross-sectional area of the blood flow path will become smaller, resulting in an increase in blood flow velocity and hence an increase in pressure loss. In the blood oxygenator of the present invention, therefore, the blood introduced through the blood inlet is distributed to two or more flow paths. This makes it possible to reduce the velocity of the blood flowing through each contact chamber and thereby decrease the pressure loss.

The hollow fibers contained in the blood oxygenator of the present invention may comprise any of various types of hollow fibers, and examples thereof include hollow fibers made of a homogeneous or porous membrane of such material as cellulosics, polyolefins, polysulfones, polyvinyl alcohol, silicone resins, PMMA and the like. However, hollow fibers made of a porous polyolefin membrane are preferred because of their excellent durability and gas permeability. Especially preferred are hollow fibers made of a membrane which comprises fibrils stacked in layers between both surfaces and nodes fixing the respective ends of the fibrils and, therefore, has micropores formed of the spaces between the fibrils and interconnected so as to extend from one surface to the other. As an example of such hollow fibers, there are polypropylene hollow fibers commercially available from Mitsubishi Rayon Co., Ltd. under the trade name of Polypropylene Hollow Fiber KPF.

The fastening members may conveniently be formed in the same manner as in the manufacture of so-called hollow-fiber filter modules using hollow fibers. Specifically, this can be accomplished by using a potting material having good adhesion properties (such as a polyurethane resin) and molding it integrally with the hollow fibers and the partitioning members.

The blood oxygenator of the present invention may be combined with a heat exchanger for blood which is disposed upstream or downstream of the blood oxygenator.

Figure 3:
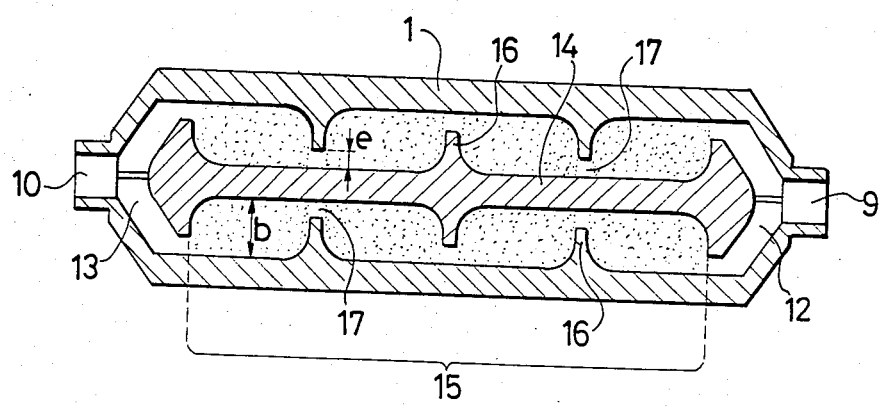
FIG. 3 is a longitudinal sectional view of another embodiment of the blood oxygenator of the present invention.
Figure 4:
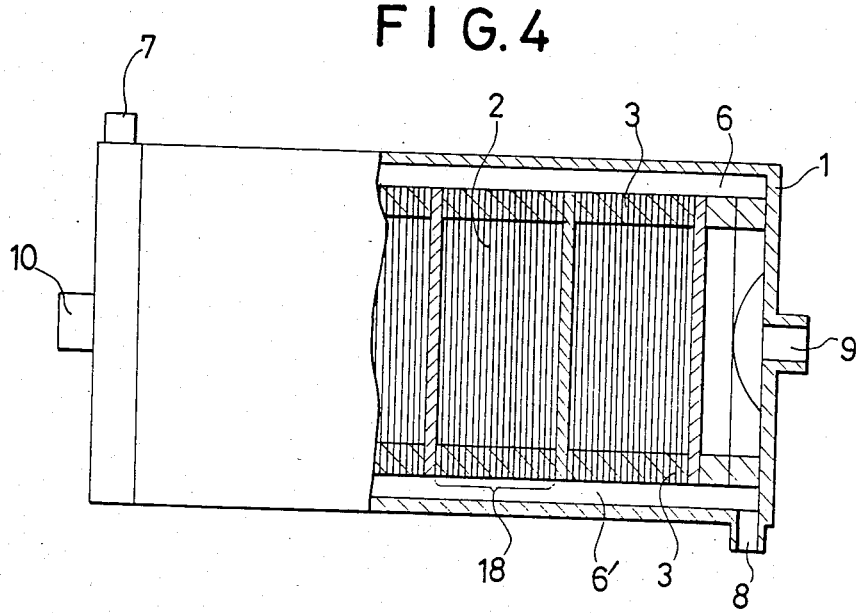
FIG. 4 is a partially cutaway plan view of the blood oxygenator of FIG. 3.

The blood oxygenator shown in FIGS. 3 and 4 is a modification of the blood oxygenator of FIG. 1 which has been described hereinabove. In this blood oxygenator, the cavity of the housing 1 is divided by a single partitioning member 14 to form two contact chambers 15 arranged in parallel. The housing 1 and the partitioning member 14 are provided with baffles (or projections) 16, so that each contact chamber 15 does not comprise a simple sheet-like space. More specifically, each contact chamber 15 has a plurality of blood flow channels 17 formed by the baffles 16 so as to narrow the blood flow path in a direction perpendicular to the direction of blood flow and the direction of the bundle of hollow fibers (hereinafter referred to as the direction of the thickness of the contact chamber), and a plurality of compartments 18 separated by these blood flow channels 17 and containing hollow fibers 2. In this embodiment, each contact chamber 15 is divided into four compartments 18 by three blood flow channels 17. Although it is desirable from the viewpoint of oxygenation rate to increase the number of compartments, each contact chamber should preferably be divided into two to six compartments in view of the pressure loss and the ease of assembly.

The baffles 16 may have any of various cross-sectional shapes including that shown in FIG. 3, provided that they can narrow the blood flow channels 17 in the direction of the thickness of the contact chamber 15. However, baffles having a curved cross section as shown in FIG. 3 are preferably used in order to avoid channeling of the blood. The purpose of the baffles 16 provided in each contact chamber 15 is to produce turbulences of the blood flow in the direction of the thickness of the contact chamber 15 and thereby prevent channeling of the blood. As shown in FIG. 3, the manner in which each contact chamber 15 is narrowed by the baffles 16 in the direction of the thickness thereof should preferably be such that adjacent blood flow channels are alternately formed on the upper and lower sides. In order to achieve the effects of the blood flow channels 17, the thickness (e) of the blood flow channels 17 should preferably be equal to or smaller than one-half the thickness (b) of the compartments 18. By providing the baffles 16, the thickness (b) of the compartments 18 can be made larger than the thickness (a) of the contact chambers shown in FIG. 1.

Figure 5:
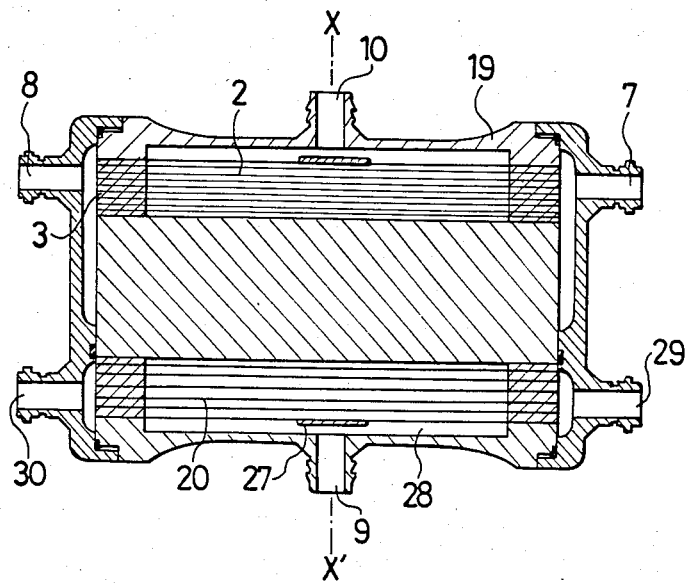
FIG. 5 is a longitudinal sectional view of still another embodiment of the blood oxygenator of the present invention.
Figure 6:
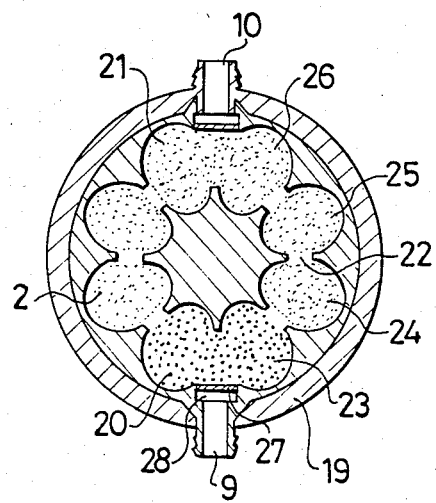
FIG. 6 is a cross-sectional view taken along line X-X' of FIG. 5.

FIGS. 5 and 6 show still another embodiment of the blood oxygenator of the present invention. This blood oxygenator is constructed in such a way that, in addition to the bundles of hollow fibers 2 for gas exchange use, bundles of hollow fibers 20 for heat exchange use are also contained in a cylindrical housing 19. As shown in FIG. 6, contact chambers 21 are disposed so as to form two circular arcs along the sidewall of the cylindrical housing 19 and extend from a blood inlet 9 provided in the sidewall of the cylindrical housing 19 to a blood outlet 10 provided on the opposite side thereof. Also in this embodiment, each contact chamber 21 is divided into a plurality of compartments 23 to 26 by blood flow channels 22 narrowed in the direction of the thickness of the contact chamber. Similar to the preceding embodiment, the blood flow channels 22 make it possible to prevent channeling of the blood flow. Although the embodiment shown in FIG. 6 includes two contact chambers each having four compartments connected in series (thus totaling eight compartments), the number of compartments provided in each contact chamber may be two or more.

Immediately after blood is introduced through the blood inlet 9 into the first compartment of each contact chamber, the blood may flow slightly in oblique directions. Accordingly, as shown in FIG. 6, baffles 27 are preferably provided in order to prevent the blood introduced through the blood inlet 9 from flowing in radial directions. The functionality of the blood oxygenator can be further improved by providing it with a blood distribution chamber 28.

Where each contact chamber has three or more compartments, one or two compartments adjacent to the blood inlet 9 or the blood outlet 10 may be packed with a bundle of tubules or hollow fibers for heat exchange use, in place of the bundle of hollow fibers for gas exchange use, so as to function as a heat exchange chamber or chambers. In this blood oxygenator, the compartment 23 contains a bundle of hollow fibers for heat exchange use while each of the compartments 24 to 26 contains a bundle of hollow fibers for gas exchange use. In FIG. 6, the bundle of hollow fibers for heat exchange use and the bundles of hollow fibers for gas exchange use are disposed so as to be perpendicular to the plane of the drawing (or parallel to the longitudinal axis of the housing 19). The opposite open ends of the hollow fibers for heat exchange use communicate with a heat exchange medium inlet 29 and a heat exchange medium outlet 30, respectively.

Although metallic tubules having good thermal conductivity may be used as the tubules for heat exchange use, it is preferable to use hollow fibers of plastic material having an internal diameter of 5 to 1,000 µm and a wall thickness of about 2 to 20 µm. For example, there may be used hollow fibers made of a non-porous membrane of polyethylene or polypropylene. Alternatively, hollow fibers made of a porous membrane may also be used, provided that the membrane has no pores extending from one surface to the other.

In this blood oxygenator, the blood introduced through the blood inlet 9 is distributed to the two compartments 23 adjacent to the blood inlet 9. Then, in each contact chamber, the blood flows successively through the compartments 24, 25 and 26 in the circumferential direction of the cylindrical housing 19. On the other hand, the gas flows through the bores of the hollow fibers in the axial direction of the cylindrical housing. Thus, the blood and the gas flow in directions substantially perpendicular to each other and come into contact to effect gas exchange therebetween.

Figure 7:
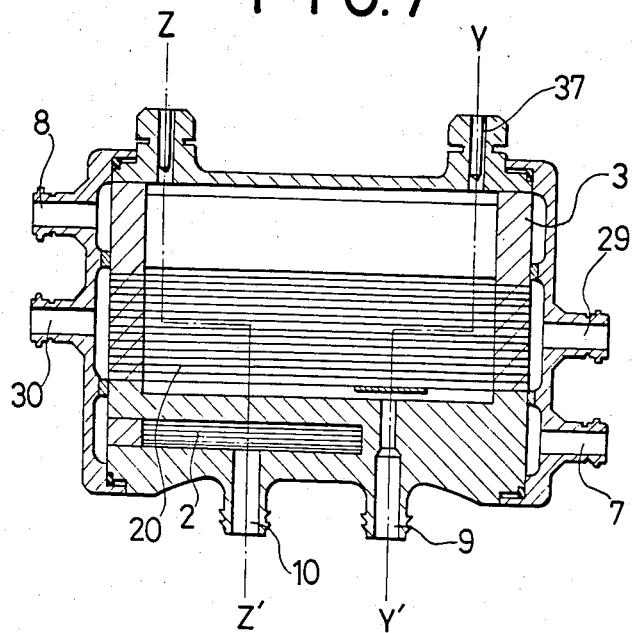
FIG. 7 is a longitudinal sectional view of a further embodiment of the blood oxygenator of the present invention.
Figure 8:
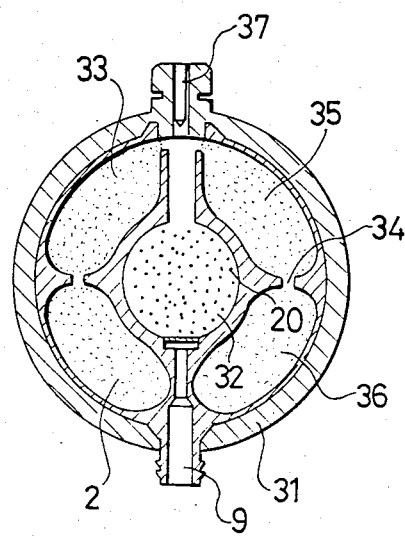
FIGS. 8 and 9 are cross-sectional views taken along line Y-Y' and line Z-Z', respectively, of FIG. 7.
Figure 9:
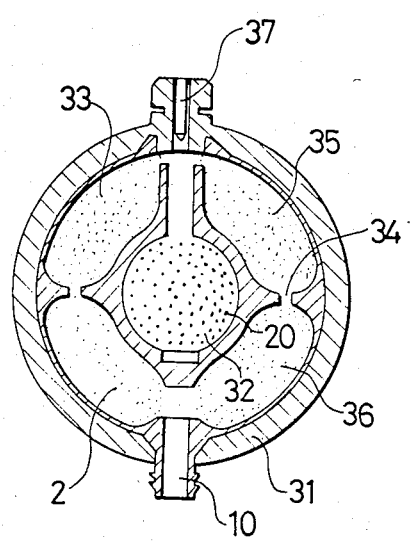

The embodiment shown in FIGS. 7 to 9 is a modification of the blood oxygenator shown in FIGS. 5 and 6. In this embodiment, the blood inlet 9 and the blood outlet 10 are disposed on the same side of the sidewall of the cylindrical housing 31, and a heat exchange chamber 32 is provided in the center of the housing 31.

Blood is introduced through the blood inlet 9 into the heat exchange chamber 32 containing a bundle of hollow fibers 20 for heat exchange use, where it undergoes heat exchange with the heat exchange medium flowing through the bores of the hollow fibers for heat exchange use. Then, the blood is distributed to two contact chambers 33 disposed in parallel, fed to the space on the outside of the hollow fibers for gas exchange use, and conducted toward the blood outlet 10, during which it undergoes oxygen-carbon dioxide exchange with the oxygen or oxygen-containing gas flowing through the bores of the hollow fibers for gas exchange use. The resulting oxygenated blood is withdrawn from the blood outlet 10.

In order to prevent channeling of the blood, it is preferable that, similar to the blood oxygenator shown in FIGS. 5 and 6, each of the contact chambers 33 disposed so as to form two circular arcs along the sidewall of the cylindrical housing be divided into a plurality of compartments 35, 36 by blood flow channels 34.

Although the heat exchange chamber 32 contains a bundle of hollow fibers for heat exchange use in this embodiment, it is also feasible that the heat exchange chamber 32 contain a bundle of hollow fibers for gas exchange use and that the two compartments adjacent to the blood outlet 10 contain a bundle of hollow fibers for heat exchange use.

If desired, this blood oxygenator may be provided with venting devices 37 which are positioned in the sidewall of the housing on substantially the opposite side of the blood inlet 9 and the blood outlet 10. These venting devices 37 communicate with the heat exchange chamber 32 and the contact chambers.

Although it is preferable to provide two venting devices as shown in the embodiment of in FIGS. 7 to 9, it is possible to provide only one venting device. The blood oxygenator should preferably be installed in such a way that the venting devices are positioned on the upper side thereof. Then, any gas entrapped in the blood accumulates at the top of the cavity owing to the difference in specific gravity between gas and blood and easily escapes from the housing through the venting devices 37.

The venting devices 37 can include a venting member made of any material that is impermeable to blood, but permeable to gases. For example, there may be used porous or homogeneous membranes of such material as cellulosics, polyolefins, PMMA and silicone. Especially preferred are porous polyolefin membranes including hollow fibers commercially available from Mitsubishi Rayon Co., Ltd. under the trade names of Polypropylene Hollow Fiber KPF and Polyethylene Hollow Fiber EHF.

In the blood oxygenators shown in FIGS. 5 to 9, bundles of hollow fibers for gas exchange use and, if present, bundles of hollow fibers for heat exchange use can be disposed within a cylindrical housing in a well-balanced manner, which greatly facilitates potting of the hollow fibers and attachment of end caps to the housing. In addition, the improved strength of the housing itself makes it possible to make lightweight and compact blood oxygenators.

Moreover, since the blood introduced through a single blood inlet is distributed to multiple channels constituting at least one half the length of the blood flow path from the blood inlet to the blood outlet, the average flow rate is reduced to about one-half, resulting decrease in flow resistance and hence a decrease in pressure loss.

Furthermore, if venting devices are provided as shown in the blood oxygenator of FIGS. 7 to 9, any gas entrapped in the blood accumulates at the top of the cavity of the housing and easily escapes to the outside through the venting devices, thus preventing blood coagulation or similar problems due to the retention of gas bubbles.

What is claimed is:

1. A blood oxygenator comprising:
a housing having a plurality of contact chambers therein, a blood inlet, a blood outlet, a gas inlet, and a gas outlet, said plurality of chambers communicating respectively with said blood inlet and said blood outlet and forming separate blood flow paths between said blood inlet and said blood outlet, said oxygenator comprising means downstream from said blood inlet for separating blood into separate but substantially equal volumes of blood and for introducing said separate but substantially equal volumes, respectively, into said plurality of chambers; and
a bundle or bundles of hollow fibers of a composition suitable for blood-gas oxygen exchange and being disposed in each said chamber substantially perpendicular to the direction of blood flow therethrough, opposite ends of said hollow; fibers respectively communicating with said gas inlet and said gas outlet.

2. The blood oxygenator of claim 1, wherein said housing has a cylindrical shape, said blood inlet and said blood outlet are provided in the sidewall of said cylindrical housing, said gas inlet and said gas outlet are provided in the opposite end surfaces of said cylindrical housing, said contact chambers are disposed longitudinally in said cylindrical housing and form two substantially semi-circular arcs along the sidewall of said cylindrical housing, said bundle or bundles of hollow fibers for gas exchange use is disposed substantially parallel to the longitudinal axis of said cylindrical housing, and each of said contact chambers is divided into a plurality of compartments by a plurality of baffles extending substantially radially with respect to said cylindrical housing so as to form a plurality of blood flow channels.

3. The blood oxygenator of claim 2 wherein some of said compartments contain a bundle of tubules for heat exchange use disposed in the same manner as said bundle or bundles of hollow fibers for gas exchange use and the opposite open ends of said tubules for heat exchange use communicate with a heat exchange medium inlet and a heat exchange medium outlet provided in the opposite end surfaces of said cylindrical housing.

4. The blood oxygenator of claim 3 wherein said tubules for heat exchange use comprise hollow fibers having an internal diameter of 5 to 1,000 μm and a wall thickness of 2 to 20 μm.

5. The blood oxygenator of claim 2, wherein a heat exchange chamber is positioned in the center of said cylindrical housing and contains a bundle of tubules for heat exchange use disposed in the same manner as said bundle or bundles of hollow fibers for gas exchange use, and wherein said blood inlet communicates with each of said contact chambers through said heat exchange chamber, and the opposite open ends of said tubules for heat exchange use communicate with a heat exchange medium inlet and a heat exchange medium outlet provided in the opposite end surfaces of said cylindrical housing.

6. The blood oxygenator of claim 5 wherein said blood inlet and said blood outlet are positioned on substantially the same side of the circumference of said cylindrical housing and at least one venting device is provided on the opposite side thereof so as to communicate with said heat exchange chamber.

7. The blood oxygenator of claim 1, wherein said plurality of contact chambers are disposed in stacked relationship.

8. The blood oxygenator of claim 7 wherein each of said contact chambers is divided into a plurality of compartments with the interposition of blood flow channels narrowed by baffles disposed so as to be substantially parallel to said bundle or bundles of hollow fibers.

9. The blood oxygenator of claim 8 wherein each of said contact chambers is divided into two to six compartments.

10. The blood oxygenator of claim 9 wherein the degree of packing of said hollow fibers for gas exchange use in each of said contact chambers ranges from 20 to 40%.

* * * * *